United States Patent
Gande et al.

(10) Patent No.: US 11,918,559 B2
(45) Date of Patent: *Mar. 5, 2024

(54) REDUCED DOSE METAXALONE FORMULATIONS

(71) Applicant: Primus Pharmaceuticals, Inc., Scottsdale, AZ (US)

(72) Inventors: Mukteeshwar Gande, Denville, NJ (US); Robert M. Levy, Cave Creek, AZ (US)

(73) Assignee: Primus Pharmceuticals, Inc., Scottsdale, AZ (US)

(*) Notice: Subject to any disclaimer, the term of this patent is extended or adjusted under 35 U.S.C. 154(b) by 0 days.

This patent is subject to a terminal disclaimer.

(21) Appl. No.: 18/197,100

(22) Filed: May 14, 2023

(65) Prior Publication Data
US 2023/0310387 A1 Oct. 5, 2023

Related U.S. Application Data

(63) Continuation of application No. 16/524,952, filed on Jul. 29, 2019.

(60) Provisional application No. 62/866,356, filed on Jun. 25, 2019.

(51) Int. Cl.
| A61K 31/421 | (2006.01) |
| A61K 9/00 | (2006.01) |
| A61K 9/20 | (2006.01) |
| A61K 9/48 | (2006.01) |

(52) U.S. Cl.
CPC .......... *A61K 31/421* (2013.01); *A61K 9/0053* (2013.01); *A61K 9/2013* (2013.01); *A61K 9/4858* (2013.01)

(58) Field of Classification Search
CPC .................................................. A61K 31/421
See application file for complete search history.

(56) References Cited

U.S. PATENT DOCUMENTS

| 3,062,827 A | 11/1962 | Lunsford |
| 2005/0276844 A1* | 12/2005 | Spireas ................ A61K 9/2031 |
| | | 424/464 |

FOREIGN PATENT DOCUMENTS

| WO | WO 2004/019937 | 3/2004 |
| WO | WO2009085637 | * 7/2009 |

OTHER PUBLICATIONS

Metaxalone Tablets for oral use; Highlights of Prescribing Information; CorePharma, LLC, 2015; 6 pp.
Metaxalone FDA Chemistry Review, Center for Drug Evaluation and Research, Reviewed Apr. 21, 2015, 76 pp.
Metaxalone FDA Medical Review{s), Center for Drug Evaluation and Research, Reviewed May 15, 2015, 94 pp.
Metaxalone FDA Clinical Pharmacology and Biopharmaceutics Review(s), Center for Drug Evaluation and Research, Reviewed Apr. 7, 2015, 110 pp.
Skelaxin Prescribing Information, King Pharmaceuticals, Apr. 2008, 1 pg.
USP Metaxalone Tablets.Official Monographs, 2015, pp. 7432-7433.
*King Pharmaceuticals, Inc., et al.* v. *Corepharma, LLC*, Civil Action No. 10-1878 {GEB-DEA), Memorandum Opinion, May 7, 2010, 10 pp.
U.S. Appl. No. 16/524,952, 132 Declaration of Mukteeshwar Gande (Feb. 27, 2020).
U.S. Appl. No. 16/524,952, 132 Declaration of Ryan Hartung (May 11, 2022).
U.S. Appl. No. 16/524,952, 132 Declaration of Karol Pencina (Dec. 29, 2022).

* cited by examiner

*Primary Examiner* — Rei Tsang Shiao
(74) *Attorney, Agent, or Firm* — Clark G. Sullivan

(57) ABSTRACT

Oral dosage forms of metaxalone having improved bioavailability in the fed and fasted states, including dosage forms that employ a reduced dose based on such improved bioavailability.

15 Claims, 1 Drawing Sheet

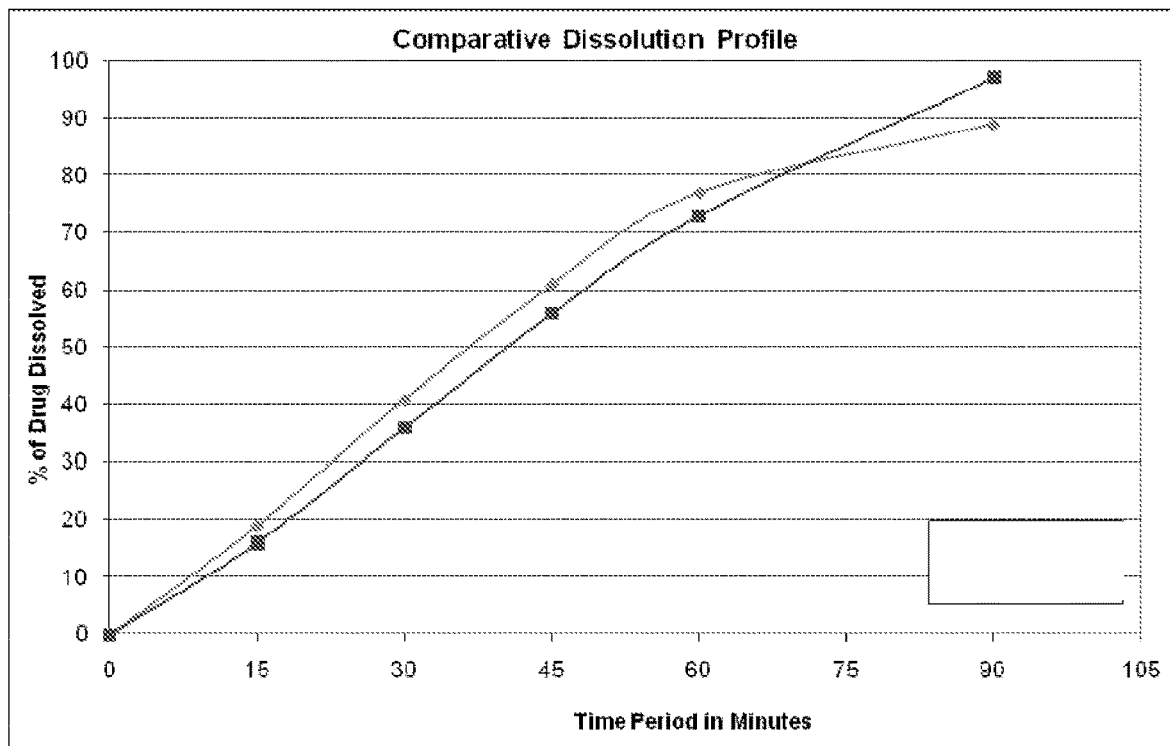

REDUCED DOSE METAXALONE FORMULATIONS

FIELD OF THE INVENTION

The present invention relates to oral dosage forms of metaxalone having improved bioavailability in the fed and fasted states, reduced food effect and the dose reduction attendant to such improved bioavailability.

BACKGROUND OF THE INVENTION

Metaxalone (Skelaxin®), known chemically as 5-[(3,5-dimethylphenoxy)methyl]-2-oxazolidinone, has the following chemical structure:

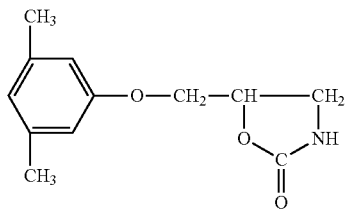 [SMILES: Cc1cc(C)cc(OCC2CNC(=O)O2)c1]

Skelaxin is indicated as an adjunct to rest, physical therapy, and other measures for the relief of discomforts associated with acute, painful musculoskeletal conditions. The mode of action of this drug has not been clearly identified but may be related to its sedative properties. Metaxalone does not directly relax tense skeletal muscles in man. The commercially available tablet contains: metaxalone, 400 and 800 mg along with inert compression tableting excipients.

Preparation of metaxalone is described in Lunsford et al., J. Am. Chem. Soc. 82, 1166 (1960) and U.S. Pat. No. 3,062,827 to Lunsford (Nov. 6, 1962, Assignee A. H. Robins), which is incorporated herein in its entirety by reference. The '827 patent discloses the compound and related species as anticonvulsants and antispasmodics; however, these activities have not been borne out by clinical experience.

The FDA-approved prescribing information for Skelaxin® indicates that the drug suffers from a significant food effect. In particular, the prescribing information reports for an 800 mg dose that "[c]ompared to fasted conditions, the presence of a high fat meal at the time of drug administration increased $C_{max}$ by 193.6% and increased AUC ($AUC_{0-t}$, $AUC_\infty$) by 146.4% and 142.2%, respectively. Time-to-peak concentration ($T_{max}$) was also delayed (4.9 h versus 3.0 h) and terminal half-life was decreased (4.2 h versus 8.0 h) under fed conditions compared to fasted conditions. This food effect generally limits the administration of the drug to the fasted state (taking on empty stomach) and significant impairs the utility of the drug.

SUMMARY OF INVENTION

The inventors have unexpectedly discovered that the food effect associated with prior art metaxalone formulations can be avoided using a formulation that meets specified dissolution criteria in 0.5% Sodium Lauryl Sulfate ("SLS") and/or Fasted State Simulated Intestinal Fluid ("FaSSIF") (pH 6.5). Thus, in a first principal embodiment the invention provides a solid oral pharmaceutical formulation comprising metaxalone and one or more pharmaceutically acceptable excipients wherein: (a) a 640 mg tablet or capsule of said formulation releases at least 50 wt %, 60 wt %, 65 wt %, or 70 wt % of its metaxalone in 60 minutes when tested in 900 mL 0.5% SLS in water in a USP Apparatus Type 2 (paddle) at 100 rpm and 37±0.5° C.; and/or (b) a 100 mg tablet or capsule of said formulation releases at least 65 wt %, 70 wt %, 75 wt %, or 80 wt % of its metaxalone in 300 minutes when tested in 900 mL of fasted state simulated intestinal fluid in a USP Apparatus Type 2 (paddle) at 50 rpm and 37±0.5° C.

This food effect associated with prior art formulations of metaxalone can also be overcome using a formulation that meets specified dissolution criteria in pH 4.5 acetate buffer dissolution medium and pH 6.0 phosphate buffer dissolution medium. Thus, in a second principal embodiment the invention provides a solid oral pharmaceutical formulation comprising metaxalone and one or more pharmaceutically acceptable excipients wherein (a) a 640 mg tablet or capsule of said formulation releases no more than 65 wt %, 60 wt %, 55 wt %, 50 wt %, or 45 wt % of its metaxalone at 90 minutes when tested in 900 mL of a pH 4.5 acetate buffer dissolution medium in a USP Apparatus Type 2 (paddle) at 100 rpm and 37±0.5° C.; and/or (b) a 640 mg tablet or capsule of said formulation releases no more than 65 wt %, 60 wt %, 55 wt %, 50 wt %, or of its metaxalone at 90 minutes when tested in 900 mL of a pH 6.0 phosphate buffer dissolution medium in a USP Apparatus Type 2 (paddle) at 100 rpm and 37±0.5° C.

The invention further provides formulations capable of achieving the dissolution criteria in the first and second principal embodiments, and thereby overcoming the food effect of prior art metaxalone formulations. Thus, in a third principal embodiment the invention provides a solid oral pharmaceutical formulation selected from a tablet and a capsule comprising from 40 to 80 wt % micronized particles of metaxalone and from 20 to 60 wt % non-micronized particles of metaxalone, wherein (a) 90% of the micronized particles of metaxalone are smaller than 500, 350, 200, 100, 75, or 50 microns when tested according to the Malvern Method; and (b) less than 10%, 5%, or 2% of the non-micronized particles are retained on a #30 sieve, and at least 25%, 35%, or 45% of the non-micronized particles of metaxalone are retained on a #120 sieve when tested by the Sieve Method.

In a fourth principal embodiment the invention provides a solid oral pharmaceutical formulation selected from a tablet and a capsule comprising (a) 640 weight parts metaxalone; and (b) from 10 to 30 weight parts propylene glycol alginate.

In a fifth principal embodiment the invention provides a method of treating musculoskeletal pain comprising administering to a patient in need thereof 640 mg of metaxalone in the formulation of any of the principal embodiments or subembodiments of the present invention, in the fasted or fed state, preferably in the fasted state.

Additional advantages of the invention are set forth in part in the description which follows, and in part will be obvious from the description or may be learned by practice of the invention. The advantages of the invention will be realized and attained by means of the elements and combinations particularly pointed out in the appended claims. It is to be understood that both the foregoing general description and the following detailed description are exemplary and explanatory only and are not restrictive of the invention, as claimed.

BRIEF DESCRIPTION OF THE FIGURES

The accompanying drawings, which are incorporated in and constitute a part of this specification, illustrate several embodiments of the invention and together with the description serve to explain the principles of the invention.

FIG. 1 is a graphical depiction of the rate of release of metaxalone from prior art Skelaxin® 800 mg tablets (diamonds) and 640 mg metaxalone tablets (squares) (manufactured according to the current invention, in sodium lauryl sulfate dissolution medium, as described in Example 5.

DETAILED DESCRIPTION

Definitions and Use of Terms

When the singular forms "a," "an" and "the" or like terms are used herein, they will be understood to include plural referents unless the context clearly dictates otherwise. Thus, for example, reference to "an excipient" includes mixtures of two or more such excipients, and the like. The word "or" or like terms as used herein means any one member of a particular list and also includes any combination of members of that list.

When used herein the term "about" or "ca." will compensate for variability allowed for in the pharmaceutical industry and inherent in pharmaceutical products, such as differences in product strength and bioavailability due to manufacturing variations and time-induced product degradation. The term allows for any variation which in the practice of pharmaceuticals would allow the product being evaluated to be considered pharmaceutically equivalent or bioequivalent, or both if the context requires, to the recited strength of a claimed product. It will be understood that all numeric values expressed in this document can be prefaced by the term "about."

As used in this specification and in the claims which follow, the word "comprise" and variations of the word, such as "comprising" and "comprises," means "including but not limited to," and is not intended to exclude, for example, other additives, components, integers or steps. When an element is described as comprising a plurality of components, steps or conditions, it will be understood that the element can also be described as comprising any combination of such plurality, or "consisting of" or "consisting essentially of" the plurality or combination of components, steps or conditions.

When ranges are given by specifying the lower end of a range separately from the upper end of the range, or specifying particular numerical values, it will be understood that a separate range can be defined by selectively combining any of the lower end variables, upper end variables, and particular numerical values that is mathematically possible. In like manner, when a range is defined as spanning from one endpoint to another, the range will be understood also to encompass a span between and excluding the two endpoints.

As used herein, "therapeutically effective amount" refers to an amount sufficient to elicit the desired biological response. The therapeutically effective amount or dose will depend on the age, sex and weight of the patient, and the current medical condition of the patient. The skilled artisan will be able to determine appropriate dosages depending on these and other factors in addition to the present disclosure.

"Pharmaceutically acceptable" means that which is useful in preparing a pharmaceutical composition that is generally safe, non-toxic and neither biologically nor otherwise undesirable and includes that which is acceptable for human or veterinary pharmaceutical use. "Pharmaceutically acceptable salts" means salts that are pharmaceutically acceptable, as defined above, and which possess the desired pharmacological activity.

When a dose of a drug or its pharmaceutically acceptable salt is described herein, it will be understood that the dose is based on the weight of the free base, excluding any hydrates or solvates thereof, unless the description states that the dose is based on the weight of the salt, hydrate or solvate.

Throughout the patent application, wherever an analysis by a method prescribed in the United States Pharmacopoeia ("USP") is prescribed, it will be understood that the analysis is performed in accordance with the USP volume in effect on Jan. 1, 2019. It will also be understood that the test need not have been performed, but that the test, if performed, would yield the claimed result. In like manner, any terms not otherwise defined herein can be defined by reference to the USP volume in effect on Jan. 1, 2019.

The term fasted state simulated intestinal fluid or "FaSSIF" refers to the following dissolution media at pH 6.5, as described in Table II by Klein S. The AAPS Journal, Vol. 12, No. 3, September 2010.

| | |
|---|---|
| sodium taurocholate | 3 mM |
| lecithin | 0.75 mM |
| NaH$_2$PO$_4$ | 4.438 g |
| NaCl | 6.186 g |
| NaOH | qs ad to pH 6.5 |
| deionized water | qs ad to 1 L |
| osmolality (mOsmol/kg) | ~270 |
| buffer capacity (mEq/pH/L) | ~12 |
| surface tension (mN/m) | 54 |

The Sieve Method refers to the method for particle size analysis described in American Society for Testing and Materials (ASTM) standard C 136 (in effect on Jan. 1, 2019). In the method a representative weighed sample is poured into the top sieve which has the largest screen openings. Each lower sieve in the column has smaller openings than the one above. At the base is a round pan, called the receiver. The column is typically placed in a mechanical shaker, such as the sonic sifter available from Endecotts (London, UK). See Endecotts website at https://www.endecotts.com/products/sieve-shakers/sonic-sifter/product-specifications/. The shaker shakes the column, usually for some fixed amount of time. After the shaking is complete the material on each sieve is weighed. The mass of the sample of each sieve is then divided by the total mass to give a percentage retained on each sieve. The size of the average particle on each sieve is then analyzed to get a cut-off point or specific size range, which is then captured on a screen.

Principal Embodiments

The invention is described herein in terms of principal embodiments and subembodiments. It will be understood that each of the subembodiments can modify any of the principal embodiments, unless such modification is logically inconsistent or expressly disallowed in this document. It will be further understood that the principal embodiments can be combined in any manner, and that the subembodiments can be combined in any manner to further modify any of the principal embodiments, unless such combination is logically inconsistent or expressly disallowed in this document.

In a first principal embodiment the invention provides a solid oral pharmaceutical formulation comprising metaxalone and one or more pharmaceutically acceptable excipients wherein: (a) a 640 mg tablet or capsule of said formulation releases at least 50 wt %, 55 wt %, 60 wt %, 65 wt %, or 70 wt % of its metaxalone in 60 minutes when tested in 900 mL 0.5% SLS in water in a USP Apparatus Type 2 (paddle) at 100 rpm and 37±0.5° C.; and/or (b) a 100 mg tablet or capsule of said formulation releases at least 65 wt %, 70 wt %, 75 wt %, or 80 wt % of its metaxalone in 300 minutes when tested in 900 mL of fasted state simulated intestinal fluid in a USP Apparatus Type 2 (paddle) at 50 rpm and 37±0.5° C.

In a second principal embodiment the invention provides a solid oral pharmaceutical formulation comprising metaxalone and one or more pharmaceutically acceptable excipients wherein (a) a 640 mg tablet or capsule of said formulation releases no more than 65 wt %, 60 wt %, 50 wt %, or 45 wt % of its metaxalone at 90 minutes when tested in 900 mL of a pH 4.5 acetate buffer dissolution medium in a USP Apparatus Type 2 (paddle) at 100 rpm and 37±0.5° C.; and/or (b) a 640 mg tablet or capsule of said formulation releases no more than 65 wt %, 60 wt %, 50 wt %, or 45 wt % of its metaxalone at 90 minutes when tested in 900 mL of a pH 6.0 phosphate buffer dissolution medium in a USP Apparatus Type 2 (paddle) at 100 rpm and 37±° C.

In a third principal embodiment the invention provides a solid oral pharmaceutical formulation selected from a tablet and a capsule comprising from 40 to 80 wt % micronized particles of metaxalone and from 20 to 60 wt % non-micronized particles of metaxalone, wherein (a) 90% of the micronized particles of metaxalone are smaller than 500, 350, 200, 100, 75, or 50 microns when tested according to the Malvern Method; and (b) at least 20%, 25%, 30%, or 35% of the non-micronized particles of metaxalone are retained on a #120 sieve when tested by the Sieve Method.

In a fourth principal embodiment the invention provides a solid oral pharmaceutical formulation selected from a tablet and a capsule comprising (a) 640 weight parts metaxalone; and (b) from 10 to 30 weight parts propylene glycol alginate.

In a fifth principal embodiment the invention provides a method of treating musculoskeletal pain comprising administering to a patient in need thereof 640 mg of metaxalone in the formulation of any of the principal embodiments or subembodiments of the present invention, in the fasted or fed state.

Subembodiments

The invention can further be defined in terms of various subembodiments, each of which can modify any of the principal embodiments singularly or in any combination.

In various subembodiments of the present invention a 640 mg tablet or capsule of the formulation can release at least 50 wt %, 55 wt %, 60 wt %, 65 wt %, or 70 wt % of its metaxalone in 60 minutes when tested in 900 mL 0.5% SLS in water in a USP Apparatus Type 2 (paddle) at 100 rpm and 37±0.5° C.

In a particularly preferred subembodiment a 640 mg tablet or capsule of said formulation releases at least 60 wt % of its metaxalone in 60 minutes when tested in 900 mL 0.5% SLS in water in a USP Apparatus Type 2 (paddle) at 100 rpm and 37±0.5° C.; and In other subembodiments of the present invention a 100 mg tablet or capsule of said formulation releases at least 65 wt %, 70 wt %, 75 wt %, or 80 wt % of its metaxalone in 300 minutes when tested in 900 mL of fasted state simulated intestinal fluid in a USP Apparatus Type 2 (paddle) at 50 rpm and 37±0.5° C.

In a particularly preferred subembodiment a 100 mg tablet or capsule of said formulation releases at least 75 wt % of its metaxalone in 300 minutes when tested in 900 mL of fasted state simulated intestinal fluid in a USP Apparatus Type 2 (paddle) at 50 rpm and 37±0.5° C.

In another subembodiment a 640 mg tablet or capsule of said formulation releases no more than 65 wt %, 60 wt %, 55 wt %, 50 wt %, or 45 wt % of its metaxalone at 90 minutes when tested in 900 mL of a pH 4.5 acetate buffer dissolution medium in a USP Apparatus Type 2 (paddle) at 100 rpm and 37±0.5° C.

In a particularly preferred subembodiment a 640 mg tablet or capsule of said formulation releases no more than 65% of its metaxalone at 90 minutes when tested in 900 mL of a pH 4.5 acetate buffer dissolution medium in a USP Apparatus Type 2 (paddle) at 100 rpm and 37±0.5° C.

In still another subembodiment a 640 mg tablet or capsule of said formulation releases no more than 65 wt %, 60 wt %, 55 wt %, 50 wt %, or 45 wt % of its metaxalone at 90 minutes when tested in 900 mL of a pH 6.0 phosphate buffer dissolution medium in a USP Apparatus Type 2 (paddle) at 100 rpm and 37±0.5° C.

In a particularly preferred subembodiment a 640 mg tablet or capsule of said formulation releases no more than 65%% of its metaxalone at 90 minutes when tested in 900 mL of a pH 6.0 phosphate buffer dissolution medium in a USP Apparatus Type 2 (paddle) at 100 rpm and 37±° C.

The formulations of the present invention can also be defined in terms of metaxalone particle size. In one subembodiment the formulation comprises from 40 to 80 wt % micronized particles of metaxalone and from 20 to 60 wt % non-micronized particles of metaxalone. In one particular subembodiment the formulation comprises from 30 to 50 wt % or from 35 to 45 wt % micronized particles of metaxalone and from 50 to 70 wt % or from 55 to 65 wt % non-micronized particles of metaxalone.

In one subembodiment, when the formulation is characterized based on metaxalone particle size, at least 50%, 70%, or 90% of the micronized particles of metaxalone are smaller than 200, 100, or 75 microns when tested according to the Malvern Method (i.e. laser diffraction). Alternatively or in addition, at least 30%, 40%, or 50% of the micronized particles are less than 30, or 20 microns, when tested according to the Malvern Method.

In another subembodiment, no more than 10%, 5% or 2% of the non-micronized particles are retained on a #30 sieve, and at least 15%, 25%, 35%, or 45% of the non-micronized particles of metaxalone are retained on a #120 sieve when tested by the Sieve Method. In a preferred subembodiment, at least 10% or 20% of the non-micronized particles are in addition retained on a #325 sieve when tested by the Sieve Method.

In still further embodiments the formulations of the present invention are defined based on the ingredients used to make the formulation. Thus, in one subembodiment, the formulations of the present invention comprise 640 weight parts metaxalone and from 10 to 30 weight parts or from 15 to 25 weight parts propylene glycol alginate.

In still further subembodiments of formulations containing propylene glycol alginate, the formulations comprise from 20 to 35 weight parts or from 24 to 31 weight parts lactose monohydrate; from 10 to 30 or from 15 to 25 weight parts alginic acid; from 40 to 60 weight parts or from 45 to 55 weight parts of povidone; and from 2 to 8 weight parts or from 4 to 6 weight parts of a lubricant. A preferred lubricant is magnesium stearate.

EXAMPLES

In the following examples, efforts have been made to ensure accuracy with respect to numbers (e.g., amounts, temperature, etc.) but some errors and deviations should be accounted for. The following examples are put forth so as to provide those of ordinary skill in the art with a complete disclosure and description of how the methods claimed herein are made and evaluated, and are intended to be purely exemplary of the invention and are not intended to limit the scope of what the inventors regard as their invention.

Example 1 Representative Formulation

Table 1 describes a representative batch formulation for a 640 mg tablet of the current invention:

TABLE 1

| Ingredient | Ex1a | Ex1b | Ex1c | Ex1d |
|---|---|---|---|---|
| | Quantity/Batch (kg) | | | Quantity/Batch (kg) |
| Metaxalone Micronized | 53.760 kg | 41.472 kg | 41.472 kg | 53.760 kg |
| Metaxalone | 35.840 kg | 27.648 kg | 27.648 kg | 35.840 kg |
| Lactose Monohydrate | 3.764 kg | 2.903 kg | 2.903 kg | 3.764 kg |
| FD&C Yellow #6 | 0.044 kg | 0.035 kg | 0.035 kg | 0.044 kg |
| Popylene Glycol Alginate | 2.240 kg | 1.728 kg | 1.728 kg | 2.240 kg |
| Alginic Acid | 2.240 kg | 1.728 kg | 1.728 kg | 2.240 kg |
| Providone | 6.720 kg | 5.184 kg | 5.184 kg | 6.720 kg |
| Purified Water | 22.8 kg | 17.6 kg | 17.6 kg | ≈22.8 kg |
| Magnesium Stearate | 0.672 kg | 0.518 kg | 0.518 kg | 0.672 kg |
| Total | 105.28 kg | 81.216 kg | 81.216 kg | 105.28 kg |

Example 2 Representative Metaxalone Particle Sizes

Tables 2a and 2b describes representative particle sizes for the micronized and non-micronized metaxalone particles used in the formulation of Table 1.

TABLE 2a

| | Particle Size Analysis by Malvern Method | | |
|---|---|---|---|
| | 10% of the Particles ($d_{10}$) | 50% of the Particles ($d_{50}$) | 90% of the Particles ($d_{90}$) |
| Lot2a | 0.81μ | 10.11μ | 49.91μ |

*Used in Ex1a, Ex1b, and Ex1c

TABLE 2b

| | Particle Size Analysis by Sieve Method % Retained on | | |
|---|---|---|---|
| | Sieve # 30 | Sieve # 120 | Sieve # 325 |
| Lot2b | 1% | 49% | 30% |
| Lot2c | 1% | 63% | 29% |
| Lot2d | 1% | 61% | 28% |

*Used in Ex1a, Ex1b, and Ex1c, respectively

Example 3 Representative Manufacturing Method

This example includes detailed information describing the manner in which Metaxalone Tablets 640 mg are manufactured, using the formulation and metaxalone described in Tables 1 and 2.

Granulating Solution: Povidone was dissolved by slowly adding to Purified Water while mixing using mixer at required speed.

Pre-Mixing: Metaxalone Micronized, Metaxalone, FD&C Yellow #6, Propylene Glycol Alginate, and Alginic Acid were mixed at a suitable head speed.

Wet-Granulation: To the above Pre-Mix blend, added granulating solution while mixing at suitable Head Speed.

Drying: Wet-Granulation was dried Dryer to achieve desired moisture content. Milling: Upon completion of drying process, dried granulation was milled using commuting mill.

Final-Mixing: Magnesium Stearate was added to milled blend and lubricated using suitable blender.

Compression: Final-Mix Blend was compressed into tablets using Rotary Tablet Press.

Example 4 Dissolution Test Results/Fasted State Simulated Intestinal Fluid

Tables 4a and 4b describes dissolution test results for 640 mg tablets produced by the method of Example 3 (except where otherwise noted) and 800 mg Skelaxin® tablets.

TABLE 4a

Product Strength
Parts of Tablets equivalent to contain 100 mg drug
Diss. Method
900 mL of Fasting State Simulated Intestinal Fluid, USP Apparatus 2 (Paddle) at 50 rpm

| | Skelaxin Tablets | | Metaxalone Tablets Ex4a (contains 100% Micronized Drug) | Ex4b (contains 50% micronized and 50% coarse API) | Ex4c (contains 60% micronized and 40% coarse API) | Ex4d (contains 60% micronized and 40% coarse API |
|---|---|---|---|---|---|---|
| Original Strength | | | | | | |
| | 800 mg | | 640 mg | | | |
| Number of Unit Tested | | | | | | |
| | n = 3 | n = 2 | n = 3 | n = 3 | n = 3 | n = 3 | n = 3 |
| % of Dissolution | | | | | | |
| 30 Minutes | 19.7 | 19.3 | 16.4 | 10.1 | 10.0 | 12.0 | 8.6 |
| 60 Minutes | 28.2 | 27.9 | 37.2 | 30.1 | 31.8 | 36.9 | 17.4 |
| 90 Minutes | 34.3 | 34.6 | 55.8 | 43.7 | 45.2 | 49.9 | 33.4 |
| 120 Minutes | 38.7 | 39.6 | 67.1 | 53.5 | 55.6 | 59.4 | 47.0 |
| 150 Minutes | 43.3 | 44.0 | 75.2 | 59.9 | 62.6 | 66.0 | 57.7 |
| 180 Minutes | 47.2 | 47.5 | 81.1 | 65.7 | 67.7 | 71.8 | 65.4 |
| 210 Minutes | 50.8 | 51.1 | 85.6 | 70.2 | 72.4 | 75.2 | 70.4 |
| 240 Minutes | 53.7 | 54.2 | 88.5 | 74.4 | 75.9 | 78.9 | 74.6 |
| 270 Minutes | 56.0 | 56.9 | 91.1 | 77.2 | 78.9 | 81.6 | 78.1 |
| 300 Minutes | 58.3 | 59.4 | 93.0 | 80.2 | 81.4 | 83.7 | 81.4 |

TABLE 4b

Product Strength
Parts of Tablets equivalent to contain 100 mg drug
Dissolution Method
900 mL of Fasting State Simulated Intestinal Fluid, USP Apparatus 2 (Paddle) at 50 rpm
Batch Description

| | Skelaxin Tablets | | Metaxalone Tablets Ex1a (contains 60% Micronized and 40% Coarse Drug) |
|---|---|---|---|
| Original Strength | | | |
| | 800 mg | | 640 mg |
| Unit Tested | | | |
| | n = 3 | n = 2 | N = 6 |
| % of Dissolution | | | |
| 30 Minutes | 19.7 | 19.3 | 5.1 |
| 60 Minutes | 28.2 | 27.9 | 12.7 |
| 90 Minutes | 34.3 | 34.6 | 26.3 |
| 120 Minutes | 38.7 | 39.6 | 42.7 |
| 150 Minutes | 43.3 | 44.0 | 55.1 |
| 180 Minutes | 47.2 | 47.5 | 63.4 |
| 210 Minutes | 50.8 | 51.1 | 69.6 |
| 240 Minutes | 53.7 | 54.2 | 74.6 |
| 270 Minutes | 56.0 | 56.9 | 78.2 |
| 300 Minutes | 58.3 | 59.4 | 81.7 |

Example 5 Dissolution Test Results/SLS and pH Buffers

Tables 5a and 5b and FIG. 1 describe additional dissolution test results for 640 mg tablets produced by the method of Example 3 and 800 mg Skelaxin® tablets.

TABLE 5a

Dissolution Conditions
900 mL 0.5% SLS in Water,
Apparatus II, 10 rpm
Product Description

| | Skelaxin Tablets 800 mg | Metaxalone Tablets 640 mg Ex4a | Metaxalone Tablets 640 mg Ex4d |
|---|---|---|---|
| | % of Drug Dissolved in | | |
| 15 Minutes | 19 | 27 | 11.4 |
| | 17-21 | 24-29 | 10.1-12.8 |
| | 6.1 | 7.6 | 12.0 |
| 30 Minutes | 41 | 60 | 32.9 |
| | 36-44 | 56-64 | 31.8-34.0 |
| | 5.1 | 5.0 | 3.3 |
| 45 Minutes | 61 | 85 | 51.1 |
| | 60-64 | 81-91 | 50.0-52.3 |
| | 1.9 | 3.8 | 2.3 |
| 60 Minutes | 77 | 96 | 71.1 |
| | 75-79 | 90-99 | 70.2-72.1 |
| | 1.5 | 3.2 | 1.4 |
| 90 Minutes | 89 | 98 | 91.9 |
| | 87-90 | 94-102 | 90-1-93.0 |
| | 1.1 | 2.4 | 1.7 |

TABLE 5b

Dissolution
Test Product vs Skelaxin Tablets 800 mg
Method: USP Apparatus II, 100 rpm.
37° C. ± 0.5° C. (n = 3)

| Time | 900 mL pH 4.5 Acetate Buffer | | 900 mL pH 6.8 Phosphate Buffer | |
|---|---|---|---|---|
| Points | Ex1a | Skelaxin | Ex1a | Skelaxin |
| 15 Minutes | | | | |
| Average (%) | 4.6 | 8.0 | 3.1 | 6.7 |
| Range (%) | 4.3-5.0 | 7.9-8.3 | 2.8-3.5 | 6.2-7.7 |
| RSD (%) | 7.6 | 2.5 | 11.7 | 12.5 |
| 30 Minutes | | | | |
| Average (%) | 11.3 | 19.8 | 6.6 | 15.0 |
| Range (%) | 11.0-11.6 | 19.4-20.4 | 5.9-7.4 | 14.3-15.8 |
| RSD (%) | 2.9 | 2.7 | 11.5 | 4.9 |
| 45 Minutes | | | | |
| Average (%) | 19.7 | 30.0 | 11.2 | 24.6 |
| Range (%) | 18.7-21.3 | 29.6-30.6 | 9.7-13.0 | 24.1-25.6 |
| RSD (%) | 6.9 | 1.7 | 15.0 | 3.4 |
| 60 Minutes | | | | |
| Average (%) | 27.9 | 38.0 | 15.0 | 32.2 |
| Range (%) | 27.0-29.7 | 37.8-38.4 | 12.9-17.5 | 32.2-32.4 |
| RSD (%) | 5.3 | 0.8 | 15.4 | 0.4 |
| 90 Minutes | | | | |
| Average (%) | 40.0 | 44.5 | 23.1 | 41.7 |
| Range (%) | 39.3-40.7 | 44.3-44.7 | 21.4-25.0 | 41.2-42.1 |
| RSD (%) | 1.8 | 0.4 | 7.9 | 1.1 |
| 120 Minutes | | | | |
| Average (%) | 46.1 | 47.9 | 30.4 | 44.5 |
| Range (%) | 46.0-46.3 | 47.8-48.2 | 29.3-32.2 | 44.4-44.7 |
| RSD (%) | 0.3 | 0.5 | 5.1 | 0.3 |

Example 6 Bioequivalence Test Results

A randomized, single-dose, four-way, open-label, crossover study fasted and fed study comparing 640 mg metaxalone tablets produced by the method of Example 3 was conducted with the reference listed drug, Skelaxin® Tablets, 800 mg, on 47 healthy adult volunteers (29 male, 18 female). The data of the 47 subjects who completed the fasted and fed studies were used in the calculations of pharmacokinetic results using SAS. The 90% confidence interval for the geometric mean test-to-reference area and peak concentration ratios were within the bioequivalence interval of 0.80-1.25. The 640 mg tablets were proven to be bioequivalent to Skelaxin® Tablets 800 mg under fasted and fed conditions. Results of the testing are presented in Tables 6a and 6b.

TABLE 6a

| Treatments (Dose, Dosage, Form, Route) [Product ID] | Subjects No. (M/F) Type Age: Mean (Range) | Arithmetic Mean (% CV) Pharmacokinetic Parameters[1] Median (Range) for $T_{max}$ | | | | | |
|---|---|---|---|---|---|---|---|
| | | $C_{max}$ (ng/ml) | $T_{max}$ (hr) | AUC (ng-hr/ml) | AUC (ng-hr/mL) | $T_{1/2}$ (hr) | KEL (1/hr) |
| Test A: Metaxalone 640 mg Tablets, Oral (Fasting) | 47 (29/18) Healthy Volunteers 35.3 (18-69) | 2153.22 (59.22) | 3.50 (1.50-12.00) | 15723.65 (50.87) | 16023.38 (50.23) | 5.17 (41.41) | 0.1534 (36.96) |
| Test B: Metaxalone 640 mg Tablets, Oral (Fed) | | 2684.20 (58.27) | 8.00 (3.50-24.00) | 16856.88 (51.81) | 20035.82 (43.58) | 2.07 (31.50) | 0.3699 (33.01) |

TABLE 6a-continued

| Treatments (Dose, Dosage, Form, Route) [Product ID] | Subjects No. (M/F) Type Age: Mean (Range) | Arithmetic Mean (% CV) Pharmacokinetic Parameters[1] Median (Range) for $T_{max}$ | | | | | |
|---|---|---|---|---|---|---|---|
| | | $C_{max}$ (ng/ml) | $T_{max}$ (hr) | AUC (ng-hr/ml) | AUC (ng-hr/mL) | $T_{1/2}$ (hr) | KEL (1/hr) |
| Reference C: SKELAXIN® 800 mg Tablets, Oral (Fasting) | | 2030.99 (59.95) | 3.50 (2.00-6.00) | 15925.66 (51.29) | 17838.87 (50.01) | 7.04 (41.77) | 0.1184 (47.85) |
| Reference D: SKELAXIN® 800 mg Tablets, Oral (Fed) | | 3763.86 (58.84) | 5.00 (2.50-24.00) | 22381.70 (51.27) | 22959.73 (50.83) | 4.59 (43.72) | 0.1804 (45.15) |

TABLE 6b

Metaxalone
640 mg (1 × 640 mg)
Geometric Means, Ratio of Means, and 90% Confidence Intervals
Ln-Transformed Data Bioequivalence Study
Test Product B-Fed (640 mg) vs.
Test Product A-Fasting (640 mg)
N = 47

| Parameter | Test B | Test A | % Ratio | 90% C.I. |
|---|---|---|---|---|
| $AUC_{0-t}$ | 14600.21 | 13686.84 | 106.67 | (98.35, 115.70) |
| $AUC_{0-inf}$ | 14840.39 | 13988.59 | 106.09 | 98.23, 114.57 |
| $C_{max}$ | 2207.56 | 1798.83 | 122.72 | 104.93, 143.53 |

Bioequivalence Study
Test Product B-Fed (640 mg) vs.
Reference Product C-Fasting (800 mg)
N = 47

| Parameter | Test A | Reference C | % Ratio | 90% C.I. |
|---|---|---|---|---|
| $AUC_{0-t}$ | 13686.84 | 13907.27 | 98.41 | (90.74, 106.74) |
| $AUC_{0-inf}$ | 13988.59 | 14866.84 | 94.09 | (87.12, 101.62) |
| $C_{max}$ | 1798.83 | 1735.28 | 103.66 | 88.64, 121.24 |

Bioequivalence Study
Test Product B-Fed (640 mg) vs.
Reference Product D-Fed (800 mg)
N = 47

| Parameter | Test B | Reference D | % Ratio | 90% C.I. |
|---|---|---|---|---|
| $AUC_{0-t}$ | 14600.21 | 19359.95 | 75.41 | (69.53, 81.80) |
| $AUC_{0-inf}$ | 14840.39 | 19624.22 | 75.62 | (70.02, 81.67) |
| $C_{max}$ | 2207.56 | 3046.51 | 72.46 | 61.96, 84.75) |

Bioequivalence Study
Reference Product D-Fed (800 mg) vs.
Reference Product C-Fasting (800 mg)

| Parameter | Reference D | Reference C | % Ratio | 90% C.I. |
|---|---|---|---|---|
| $AUC_{0-t}$ | 19359.95 | 13907.27 | 139.21 | (128.35, 150.99) |
| $AUC_{0-inf}$ | 19624.22 | 14866.84 | 132.00 | (122.22, 142.56) |
| $C_{max}$ | 3046.51 | 1735.28 | 175.56 | (150.11, 205.33) |

Throughout this application, various publications are referenced. The disclosures of these publications in their entireties are hereby incorporated by reference into this application in order to more fully describe the state of the art to which this invention pertains. It will be apparent to those skilled in the art that various modifications and variations can be made in the present invention without departing from the scope or spirit of the invention. Other embodiments of the invention will be apparent to those skilled in the art from consideration of the specification and practice of the invention disclosed herein. It is intended that the specification and examples be considered as exemplary only, with a true scope and spirit of the invention being indicated by the following claims.

The invention claimed is:

1. A solid oral pharmaceutical tablet consisting essentially of 640 mg of metaxalone and one or more pharmaceutically acceptable excipients, wherein the metaxalone consists essentially of from 40 to 80 wt % of a first grade of particles of metaxalone and from 20 to 60 wt % of a second grade of particles of metaxalone and 10 to 30 weight parts propylene glycol alginate, further wherein:
   a) 90% of the first grade of particles of metaxalone are smaller than 100 microns when tested according to the Malvern Method;
   b) at least 35% of the second grade of particles of metaxalone are retained on a #120 sieve when tested by the Sieve Method;
   c) the first and second grades of metaxalone cause the oral dosage form to be bioequivalent to itself under both fed and fasted conditions in terms of $AUC_{0-inf}$, wherein said bioequivalence is the 90% confidence interval for a geometric mean test-to-reference area, and whereby peak concentration ratios are within a bioequivalence interval of 0.80-1.25.

2. The solid oral pharmaceutical tablet of claim 1 wherein:
   a) 90% if the first grade of particles of metaxalone are smaller than 75 microns when tested according to the Malvern Method; and
   b) less than 5% of the second grade of particles are retained on a #30 sieve when tested by the Sieve Method.

3. An oral dosage form consisting essentially of micronized metaxalone and non-micronized metaxalone, propylene glycol alginate, and alginic acid.

4. The oral dosage form formulation of claim 3, wherein the oral dosage form is bioequivalent to itself under both fed and fasted conditions in terms of and AUC0-inf, whereby said bioequivalence is the 90% confidence interval for a geometric mean test-to-reference area, and whereby peak concentration ratios are within a bioequivalence interval of 0.80-1.25.

5. The oral dosage form of claim 3, wherein:
a) the micronized metaxalone comprises 10% 0.8111 micronized metaxalone, 50% 10.00µ micronized metaxalone, and 90% 49.91µ micronized metaxalone, and,
b) the non-micronized metaxalone comprises 1 w/w % retained Sieve #30 non-micronized metaxalone, 49-63 w/w % retained Sieve #120 non-micronized metaxalone, and 28-30% retained Sieve #325 non-micronized metaxalone.

6. The oral dosage form of claim 3, further consisting essentially of:
a) 10-30 weight parts propylene glycol alginate,
b) 20-35 weight parts lactose monohydrate,
c) 10-30 weight parts alginic acid,
d) 40-60 weight parts povidone, and,
e) 4-6 weight parts magnesium stearate.

7. The oral dosage form of claim 3, further consisting essentially of:
a) 0.064-0.0212 w/w % povidone,
b) 0.0357 w/w % lactose monohydrate,
c) 0.00638 w/w % magnesium stearate,
d) 0.021 w/w % propylene glycol alginate, and,
e) 0.021 w/w % alginic acid.

8. The oral dosage form of claim 3, further consisting essentially of 640 mg of micronized and non-micronized metaxalone.

9. The oral dosage form of claim 3, wherein the weight ratio of micronized metaxalone to non-micronized metaxalone is 60:40.

10. The oral dosage form of claim 1, consisting essentially of 40-80 wt % micronized metaxalone and 20-60 wt % non-micronized metaxalone,
a) wherein 90% of said micronized metaxalone are in the range of 50-500 microns, and,
b) wherein 2-10% of said non-micronized metaxalone are retained on a #30 sieve and 25-45% of said non-micronized metaxalone are retained on a #120 sieve.

11. The oral dosage form of claim 3, consisting essentially of 640 weight parts metaxalone and 10-30 weight parts propylene glycol alginate.

12. A tablet oral dosage form made by the following steps consisting essentially of:
a) preparing a granulating solution by dissolving povidone in purified water by mixing;
b) pre-mixing micronized and non-micronized metaxalone, propylene glycol alginate and alginic acid at a suitable head speed producing a pre-mix blend;
c) wet granulating said pre-mix blend while adding said granulating solution to said pre-mix blend producing a wet granulation product;
d) drying said wet granulation product to a predetermined moisture content producing a dried granulation product;
e) commute milling said dried granulation product producing a milled product;
f) mixing magnesium stearate into said milled product; and
g) compressing said milled product producing said tablet oral dosage form.

13. The tablet of claim 12, wherein the tablet consists essentially of:
a) 640 mg micronized and non-micronized metaxalone,
b) 10-30 weight parts propylene glycol alginate,
c) 10-30 weight parts alginic acid, and,
d) 4-6 weight parts magnesium stearate,
e) wherein said metaxalone consists essentially of 40-80 wt % micronized metaxalone and 20-60 wt % non-micronized metaxalone,
f) wherein 90% of said micronized metaxalone are in the range of 50-500 microns, and,
g) wherein 2-10% of said non-micronized metaxalone are retained on a #30 sieve and 25-45% of said non-micronized metaxalone are retained on a #120 sieve.

14. A solid oral pharmaceutical tablet consisting essentially of 640 mg of metaxalone and one or more pharmaceutically acceptable excipients, wherein:
a) the metaxalone consists essentially of from 40 to 80 wt % of a first grade of particles of metaxalone and from 20 to 60 wt % of a second grade of particles of metaxalone;
b) 90% of the first grade of particles of metaxalone are smaller than 100 microns when tested according to the Malvern Method; and
c) at least 35% of the second grade of particles of metaxalone are retained on a #120 sieve when tested by the Sieve Method.

15. The tablet of claim 14 wherein the first and second grades of metaxalone cause the oral dosage form to be bioequivalent to itself under both fed and fasted conditions in terms of $AUC_{0-inf}$, wherein said bioequivalence is the 90% confidence interval for a geometric mean test-to-reference area, and whereby peak concentration ratios are within a bioequivalence interval of 0.80-1.25.

* * * * *